US00PP36487P3

(12) United States Plant Patent
Gonzalez Castro et al.

(10) Patent No.: US PP36,487 P3
(45) Date of Patent: Feb. 25, 2025

(54) ***QUILLAJA SAPONARIA* PLANT NAMED 'DK-QSCB1326'**

(50) Latin Name: ***Quillaja saponaria* Molina**
Varietal Denomination: DK-QSCB1326

(71) Applicant: Desert King Chile S.A., Valparaiso (CL)

(72) Inventors: Javier Enrique Gonzalez Castro, Valpariso (CL); Ingrid Graciela Salgado Valdivia, Valparaiso (CL); Leandro Mauricio Padilla Iglesias, Valparaiso (CL)

(73) Assignee: Desert King Chile, S.A., Valparaiso (CL)

( * ) Notice: Subject to any disclaimer, the term of this patent is extended or adjusted under 35 U.S.C. 154(b) by 66 days.

(21) Appl. No.: 18/073,636

(22) Filed: Dec. 2, 2022

(65) Prior Publication Data

US 2024/0196770 P1 Jun. 13, 2024

(51) Int. Cl.
*A01H 5/00* (2018.01)
*A01H 6/00* (2018.01)
*A01H 6/54* (2018.01)

(52) U.S. Cl.
USPC ..... Plt./216
CPC ..... *A01H 6/00* (2018.05); *A01H 6/54* (2018.05)

(58) Field of Classification Search
USPC ..... Plt./216
CPC ..... A01H 5/00; A01H 5/12
See application file for complete search history.

(56) References Cited

U.S. PATENT DOCUMENTS 10,660,924 B2 5/2020 Iglesias et al.
11,254,699 B2 2/2022 Padilla Iglesias et al.

OTHER PUBLICATIONS

Rodriguez, Roberto R. et al., "Flora Arbórea de Chile," Editorial de la Universidad de Concepcion—Chile, pp. 302-305; 1983.
Translation of Rodriguez, Roberto R. et al., "Flora Arbórea de Chile," Editorial de la Universidad de Concepcion—Chile, pp. 302-305; 1983.
Walther, Regina U. et al., "*Quillaja saponaria* wood extract Refined processing and forestry management guarantee sustainability and ecological benefits," Compendium on Detergency—Supplement to Household and Personal Care today, n. Feb. 2011, 2011, pp. 20-22.

*Primary Examiner* — Kent L Bell
(74) *Attorney, Agent, or Firm* — King IP Law; Joshua King

(57) ABSTRACT

A new and distinct cultivar of *Quillaja saponaria* Molina plant named 'DK-QSCB1326'. The new variety reliably provides plants producing triterpenic saponins whose fractional content of R-series saponins is lower than 50% on total saponin basis. Plants were obtained by clonal micropropagation of individuals selected from a population of *Quillaja* trees grown in an ultra-high-density plantation (app. >20,000 trees/hectare). Clone plants have high vigor after 1-year of growth, producing a large number of lateral branches at the upper third of the stem. Leaves are elliptical in shape, uniform in size and the leaf blade is undulated; the margin of leaves is occasionally dentate, and the leaf apex is retuse. The resistance or susceptibility to diseases have not yet been assessed in this new variety.

15 Drawing Sheets

Latin name of the genus and species of the plant claimed: *Quillaja saponaria* Molina.

Variety denomination: 'DK-QSCB1326'.

BACKGROUND AND SUMMARY

The new *Quillaja saponaria* Molina cultivar designated as 'DK-QSCB1326' is discussed and shown herein. The new variety 'DK-QSCB1326' resulted from a selection and cloning of individuals producing saponins with not more than 50% R saponin (on total saponin basis). For some information about X saponin and R Saponin, see, e.g., Fleck, et al., *Saponins from Quillaja saponaria and Quillajabrasiliensis: Particular Chemical Characteristics and Biological Activities*, Molecules 2019, 24, 171 (Table 1 (page 4), discusses Saponins and refers to radical Ro which can be Rha (originating Rhamnosylated analogues or R-series) or Xyl (xylosylated analogues or X-series)).

The obtention process of the new variety 'DK-QSCB1326' was initiated by planting app. 60,000 different wild type *Quillaja* plant seeds grown in an ultra-high density (UHD) plantation system (U.S. Pat. No. 11,254,699 B2) started in Casablanca, Valparaiso, Chile, at the beginning of 2009. Subsequently, between 2009 and 2012, a first selection of 42 individuals was performed over the growing plants based on their vigor and afterwards, between 2012 and 2013, the 42 selected individuals were evaluated over their saponin content and composition as revealed by chromatographic analysis of the biomass extracts. After this second round of selection, the 7 selected individuals were micro propagated. The micro propagation process was performed asexually through explants in a facility located in Valparaíso, Chile. The explants obtained from the selected individuals were washed with a cleaning solution of 1% sodium hypochlorite and Tween® 20 and subsequently transferred to MS culture media supplemented with vitamins and naphthaleneacetic acid (ANA) for their propagation and in vitro growth.

Dehydration of the cuttings was avoided by placing them in moistened rooting medium within a humid enclosed chamber. Once established and multiplied in vitro, the 5 cm explants were established in substrate and treated with indole-3-butyric acid (IBA) to induce their roots generation and to initiate their acclimatization process. Subsequently, the cuttings were transplanted to plant containers with a substrate mixture and then they were covered individually with a plastic container to control humidity and kept it in greenhouse until to obtain acclimated plants to environmental conditions. Variety 'DK-QSCB1326' was selected after the above procedure and the acclimated plants were subsequently transferred to the field in a UHD plantation system in 2016. 'DK-QSCB1326' variety has been evaluated extensively over several years for performance and genetic stability. The morphological results shown in this document are based on monitoring performed from 2018 to 2024 in some cases.

'DK-QSCB1326' offers many advantages over seed-based plants and wild plants of *Quillaja saponaria* Molina that are known to Applicant. For example, 'DK-QSCB1326' has a low content of saponins belonging to the R-series, high-biomass yield, and high performance during micropropagation procedures. 'DK-QSCB1326' has high vigor after 1-year growth, producing a large number of twigs in the upper third of the stem. The leaves are undulated, elliptical in shape with margin occasionally dentate and retuse apex (versus plane, and oval to elliptical slightly elongated leaves of other cultivars such as 'DK-QSCB1348' (co-pending U.S. Plant patent application Ser. No. 18/073,639)). 'DK-QSCB1326' also shows a shorter distance between plants buds than 'DK-QSCB1348'. 'DK-QSCB1326' has a foliage of medium density at spring (September-December in Chile) having multiple semi-erect stems and poorly branched twigs.

Also, in contrast to the plants of traditional plantations and wild plants, the present cultivar 'DK-QSCB1326' is significantly greater in vigor, offering a high plant yield and a variety-specific saponin composition low in R-series saponins. The saponin content and improved plant yield offers significant advantages to growers, who require the sustainable production of plants to maintain harvest efficiency. The capability of easy cloning is important to growers, who will prefer to work with cultivars avoiding complex field managing practices, in order to guarantee subsequent crops and growing cycles.

For reference, methods associated with operation of ultra-high-density plantations can be found in U.S. Pat. No. 11,254,699 B2, and methods of extraction and purification of saponins can be found in U.S. Pat. No. 10,660,924 B2; all references are incorporated herein by reference in their entirety and for all their teachings and disclosures, regardless of where the references may appear in this application.

BRIEF DESCRIPTION OF THE FIGURES

FIG. 4A: insertion angle of the twigs in the main stem, and FIG. 4B: insertion angle of the extensions in the twigs.

DETAILED DESCRIPTION

Note: statements of characteristics herein represent exemplary observations of the cultivar herein and will vary depending on time of year, location, annual weather, etc.

Cultivar name: 'DK-QSCB1326'.

Classification:

*Family*.—Quillajaceae.

*Botanical name*.—*Quillaja saponaria* Molina.

*Common name*.—*Quillaja*, quillay.

Parentage: The parents of the variety 'DK-QSCB1326' are not known but neither the parents nor the variety 'DK-QSCB1326' were found in an uncultivated state. As discussed above, the variety was found among a large number of plants cultivated and grown in an ultra-high density (UHD) plantation system (app. >20,000 plants/hectare) started in Casablanca, Valparaiso, Chile, at the beginning of 2009, which UHD plantation was started by planting app. 60,000 seeds obtained from different wild type *Quillaja* plants.

Observation place, season, and plant age:

Growing location for the observations herein: Casablanca, Valparaíso, Chile. Average annual minimum temperature 4.2° C., average annual maximum temperature 27.6° C. (Santibáñez Q., Fernando (2017) Atlas agroclimático de Chile. Estado actual y tendencias del clima. Tomo III: Regiones de Valparaíso, Metropolitana, O'Higgins y Maule [en línea]. www.agrimed.cl/atlas/tomo3.html).

Time of year (season): Spring (southern hemisphere; September-December).

Age of plants used for this description: Between three and eight years old, the year of evaluation is indicated in each case.

Age of plants used for the photographs in the Figures: Four years old.

Type of greenhouse covering or growing structure, or field: Ultra-High Density Plantation System in open field (app. >20,000 trees/hectare).

References to morphological observations can be compared to: Rodriguez Rios, R., et al., (1983) Flora arborea de Chile, Concepcion, Chile: Universidad de Concepcion (Annex 1, *Quillaja saponaria* Molina).

References to color refer to The Royal Horticultural Society (R.H.S.) Large Colour Chart, Sixth Revised Edition, London, United Kingdom (2019).

Light: Natural.

PLANT DESCRIPTION

Tree:

*Size and growth habit*.—Vigorous tree growth under Ultra-High Density (UHD) Plantation System (U.S. Pat. No. 11,254,699 B2), average height app. 2.5 m (from base to apex). The average diameter is 3.25 cm (at 10 cm above ground). The main trunk texture is aciculate (according to data taken in year 2021).

*Growth habit*.—Upright.

*Stem color*.—Main stem color is "moderate brown" (RHS 200D to 200C) with small "light grey" (RHS N200D) speckles.

Figure 1:
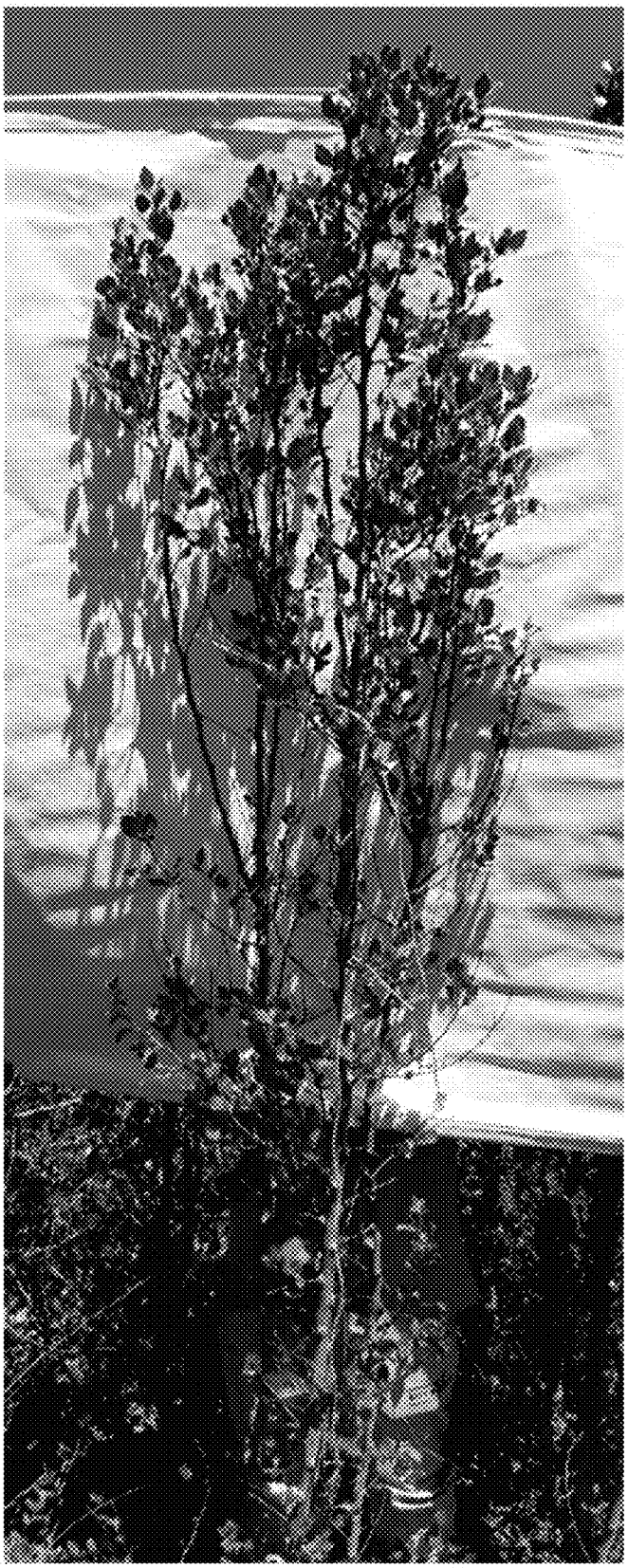
FIG. 1 is a photograph showing the upright growth habit of the variety 'DK-QSCB1326' after 4 years growing in the field.
Figure 2A:
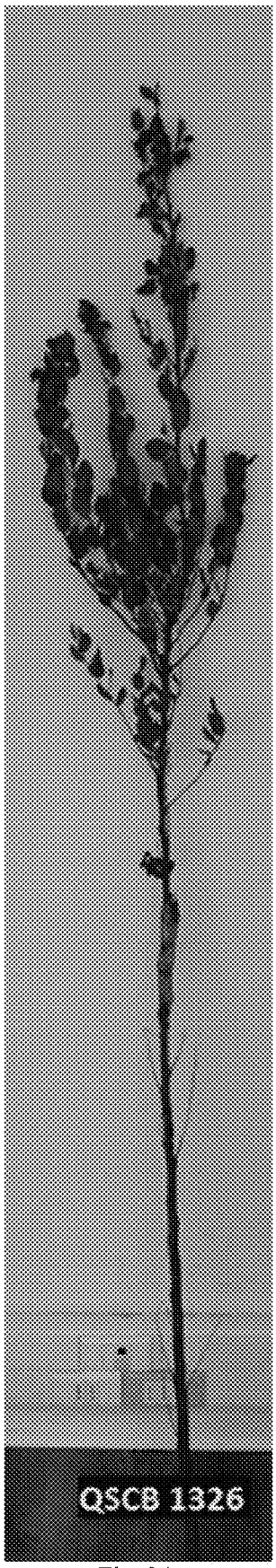
FIGS. 2A-2D are photographs of twigs of the variety 'DK-QSCB1326'. The views in the figures include: Distribution of twigs along to stem with (FIG. 2A) and without leaves (2B); a single twig picked from the stem with (FIG. 2C) and without leaves (2D). The denomination 'QSCB1326' in FIGS. 2A-2D refers to the variety 'DK-QSCB1326'.
Figure 2B:
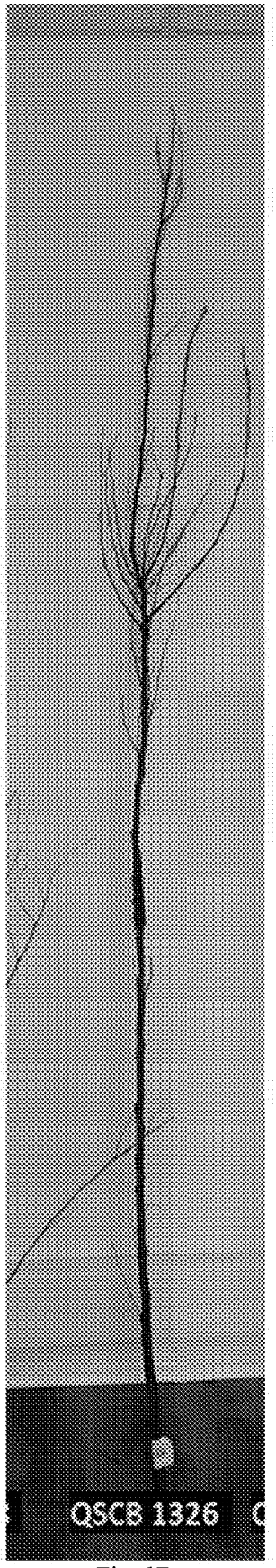
Figure 2C:
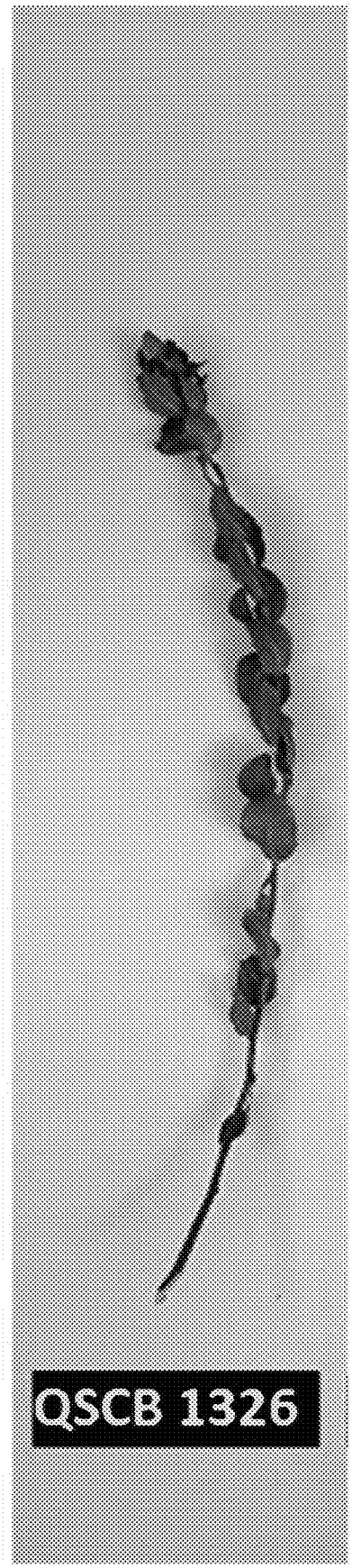
Figure 2D:
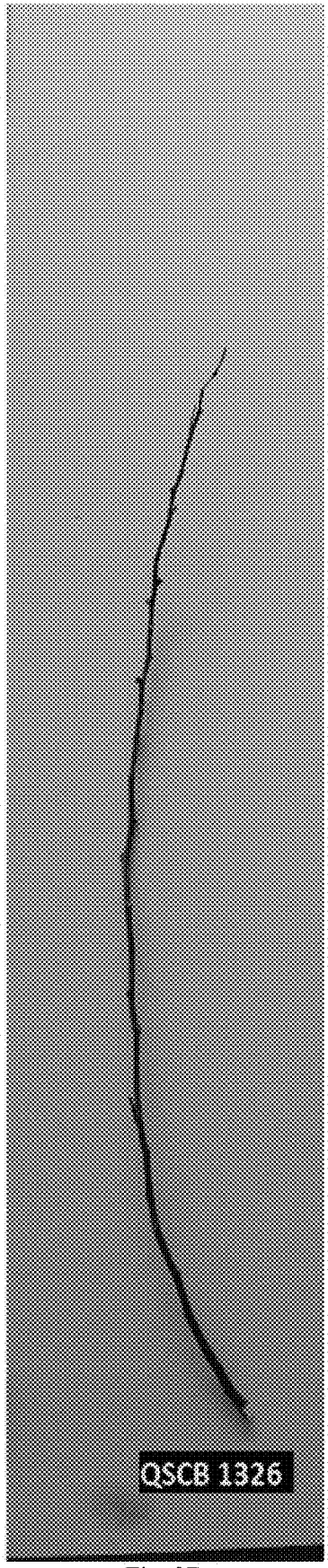
Figure 3A:
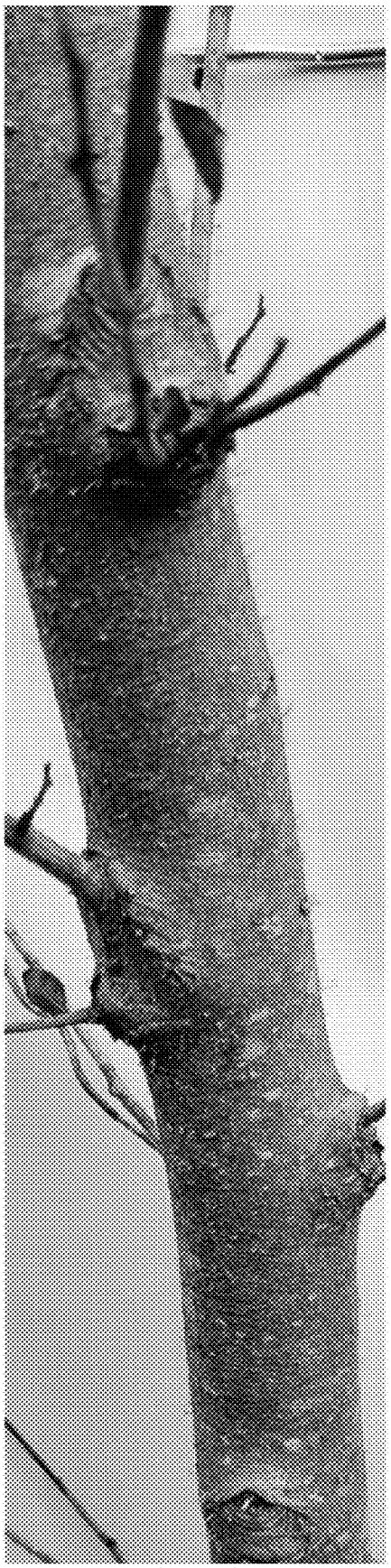
FIGS. 3A-3B are photographs of the color of the stem (FIG. 3A) and a single twig taken from the stem (FIG. 3B) of the variety 'DK-QSCB1326'.
Figure 3B:
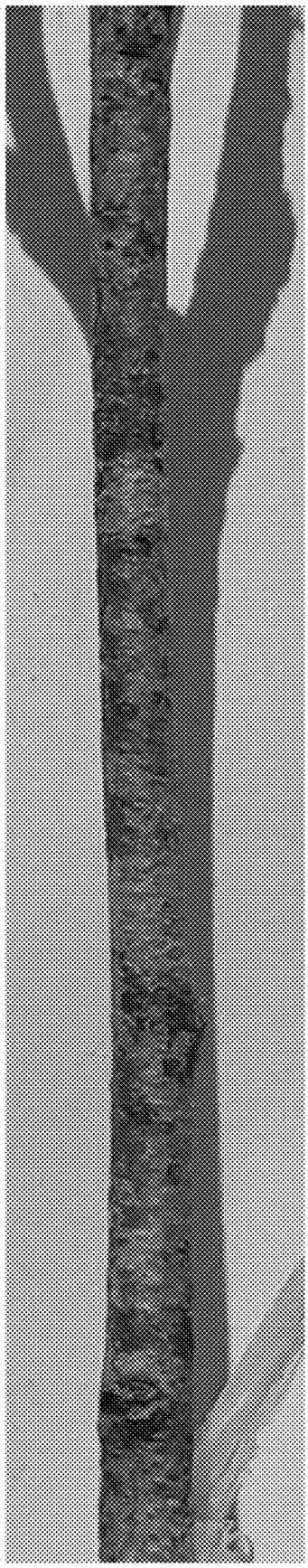
Figure 4A:
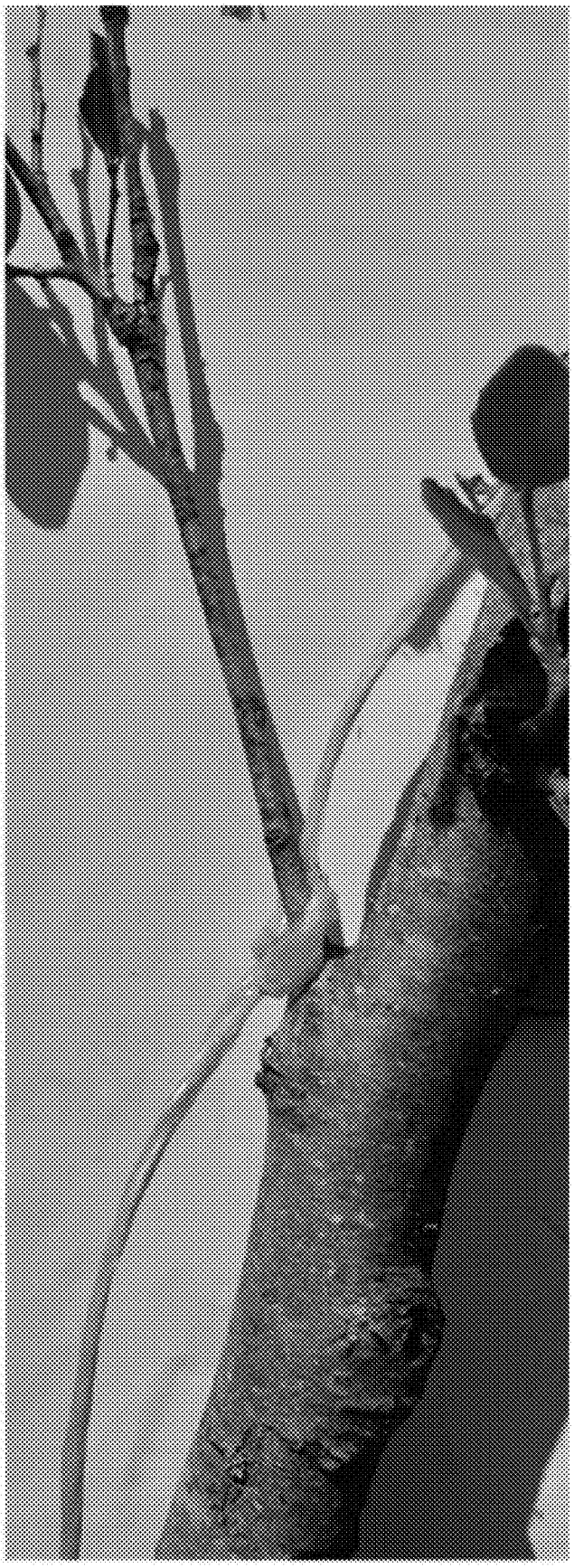
FIGS. 4A-4B are photographs of the insertion angles of the branches in the variety 'DK-QSCB1326'.
Figure 4B:
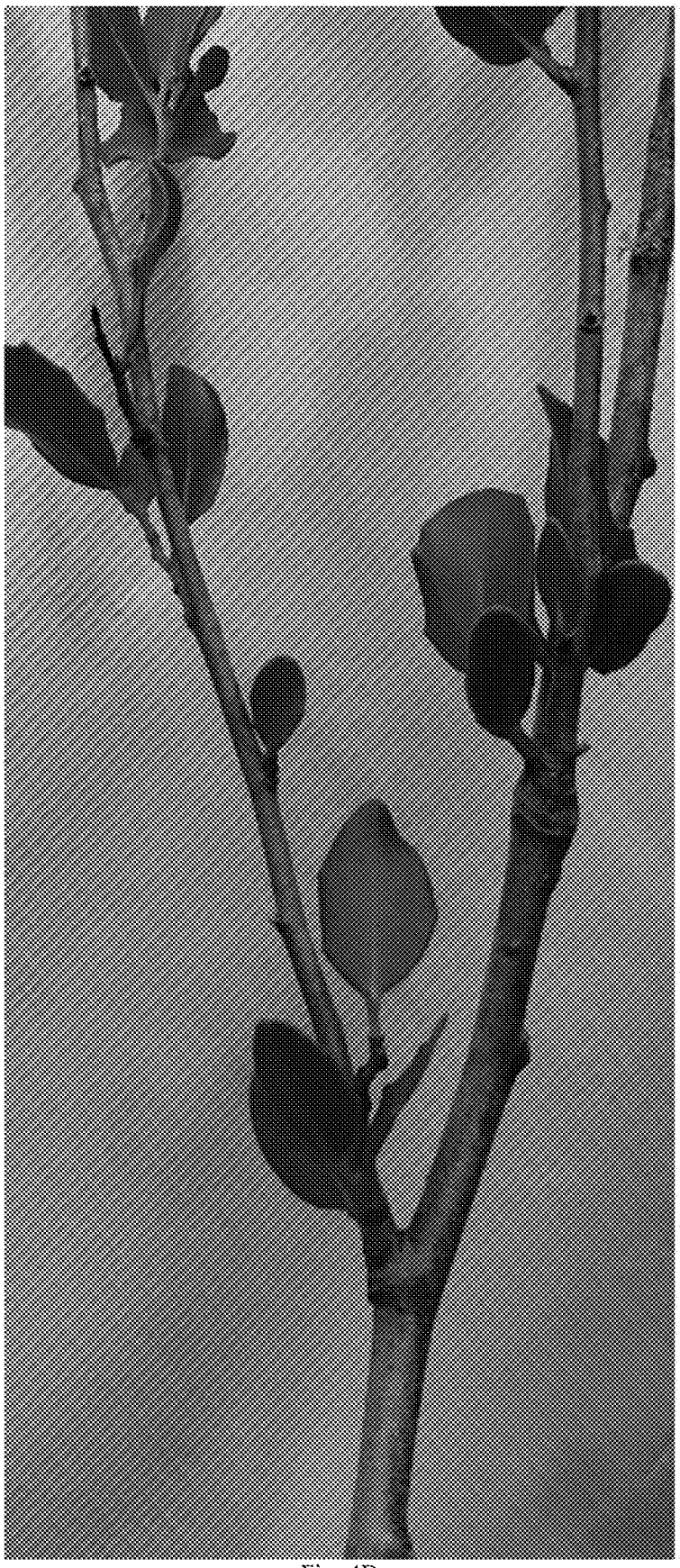

Crown:

*Crown shape*.—Slightly oblong, with slightly fastigiate branches concentrated in the upper third of the stem (FIGS. 1 and 2A). The insertion angle of the branches in stem is semi-erect (FIGS. 4A).

Crown diameter, measured at the drip-line in two dimensions is 0.56×0.61 m (according to data taken in 2024).

Foliage: The foliage is concentrated in the upper third of stem and twigs are more abundant in the upper third of branches (FIGS. 1 and 2A).

Twigs: The twigs evaluated correspond to those present in the middle third of the tree. These twigs range from 13 to 81 cm in length with a typical length of 34 cm (according to data taken in year 2020). The twigs' diameter range from 0.3 to 0.8 cm in width with a typical width of 0.5 cm (according to data taken in year 2020). The internode length ranges from 1 to 3 cm with a typical internode length of 1.6 cm (according to data taken in year 2020). The texture of twigs is aciculate.

*Twig color*.—"Light gray" (RHS N200D) blotchy patches over "greyish reddish brown to moderate brown" (RHS 200B to 200D) background (according to data taken in year 2022).

Buds: Terminal buds are absent. Axillary buds were observed in the middle and upper third of twigs during the spring and summer seasons. Their size is less than 1 mm, and their color are "Strong Yellow Green" (RHS 144 B). The shape of bud tip is pointed and their arrangement respect to twig axis is mainly aligned (according to data taken in year 2024). Due to their reduced size, the texture of axillary buds it was not possible to stablish. Floral buds are not observed after 8 years growing in the field.

Leaves: Leaf type is simple with semi-coriaceous consistency.

*Average leaf size*.—App. 3.73 cm length and 2.52 cm width.

Figure 5B:
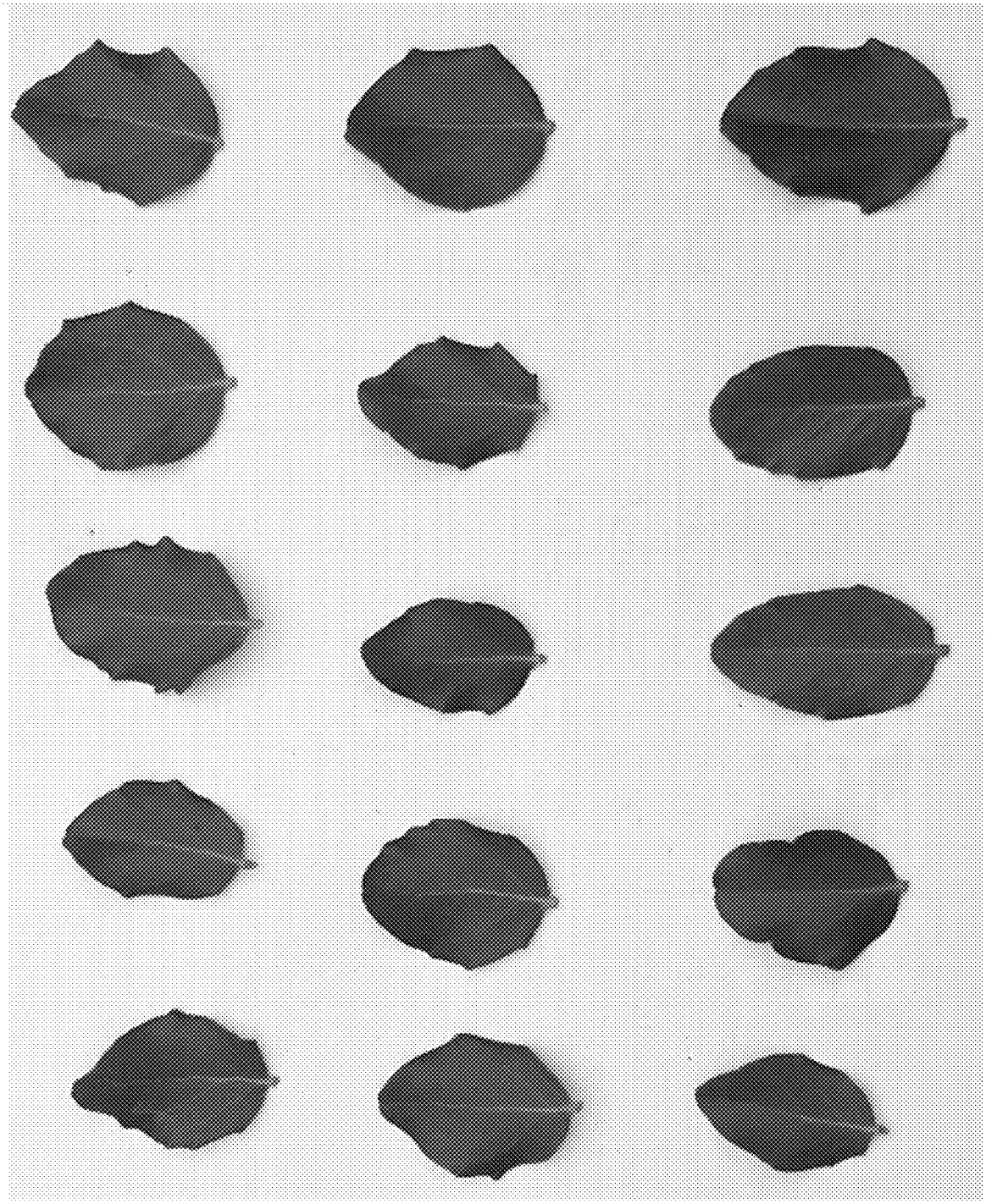
Figure 6A:
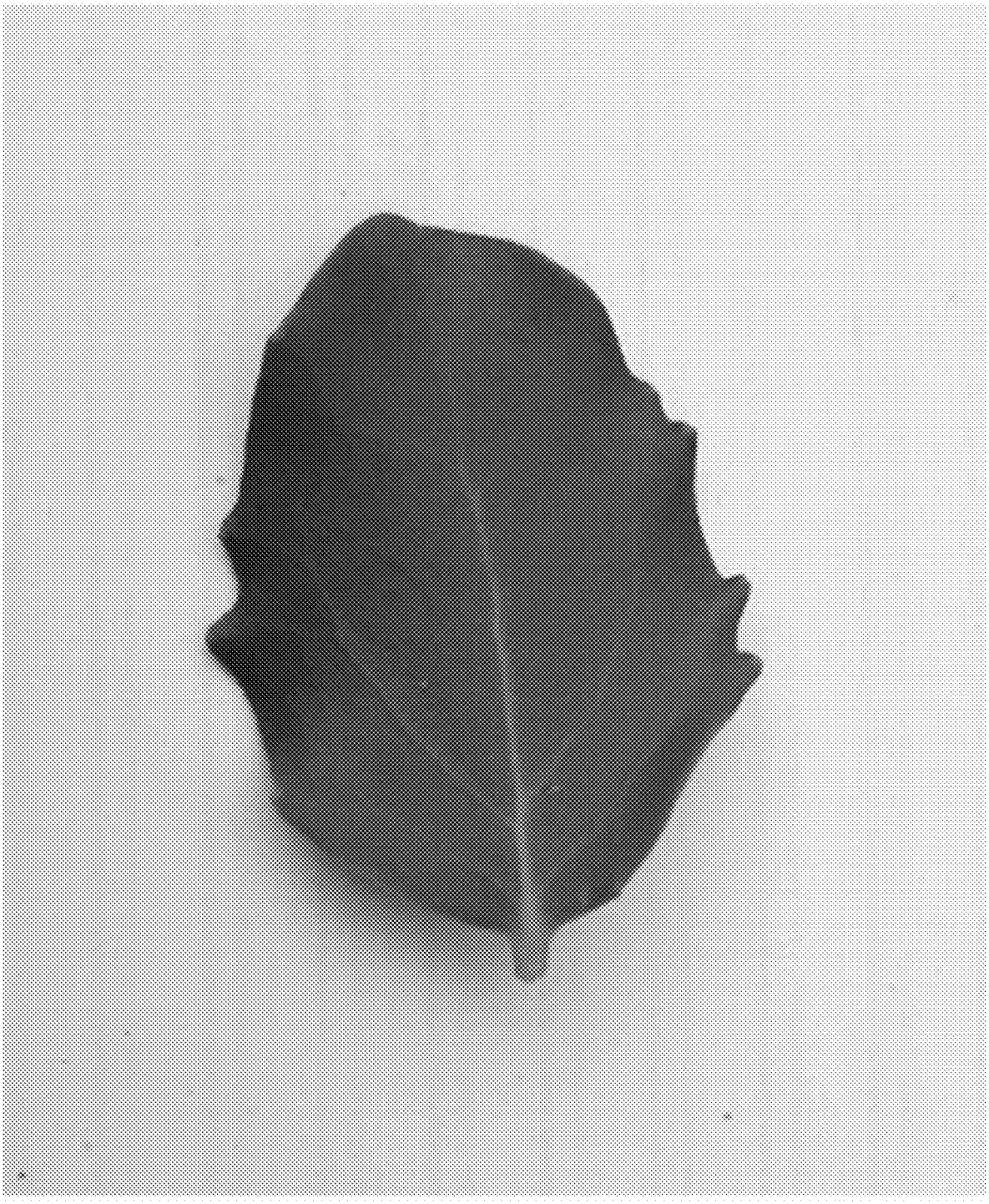
FIGS. 6A-6C are photographs of a leaf of the variety 'DK-QSCB1326'. The views in the figures include: Upperside of the leaf blade (FIG. 6A), back-side of the leaf blade (FIG. 6B) and sideview of the leaf blades (FIG. 6C).
Figure 6B:
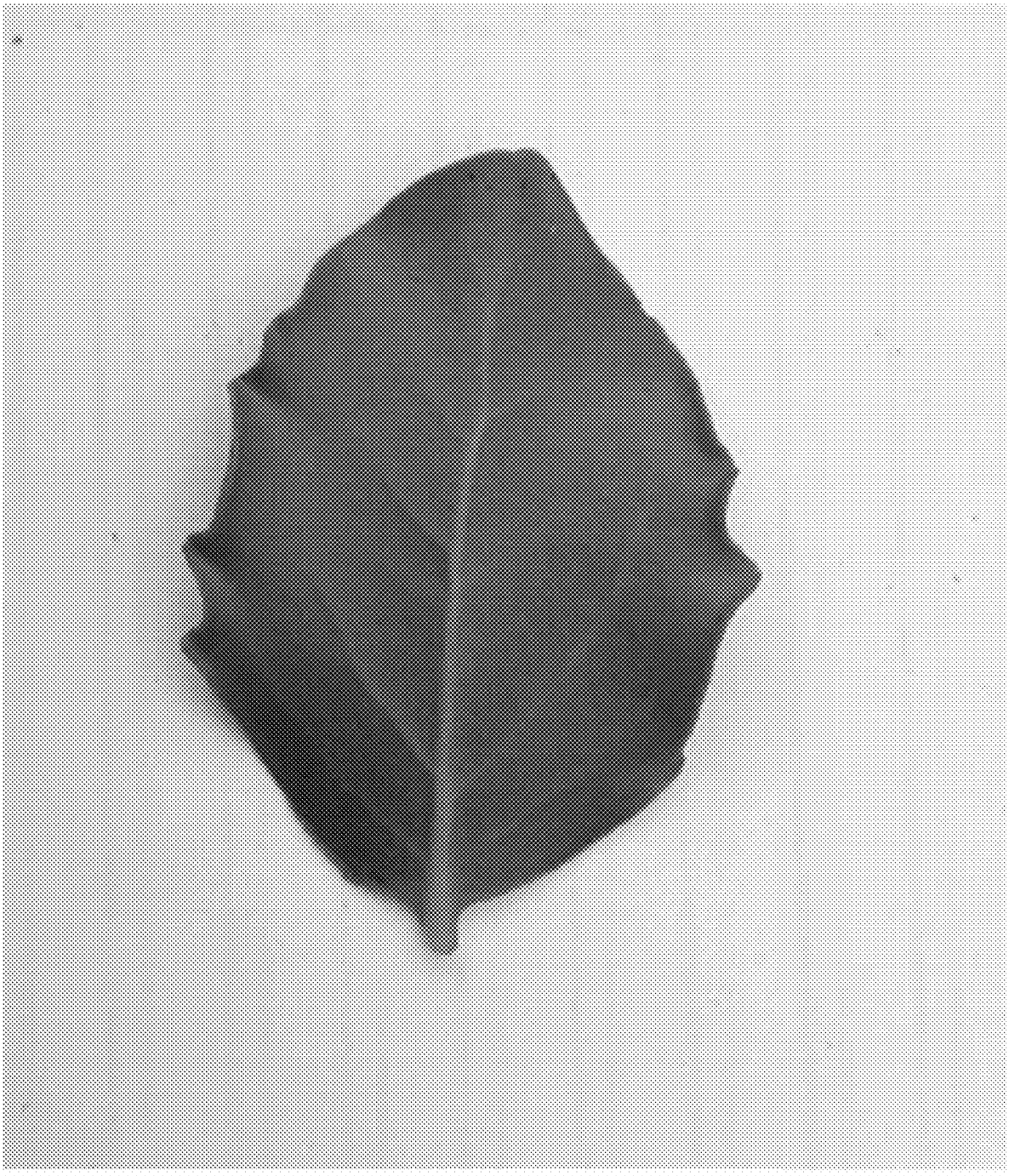
Figure 6C:
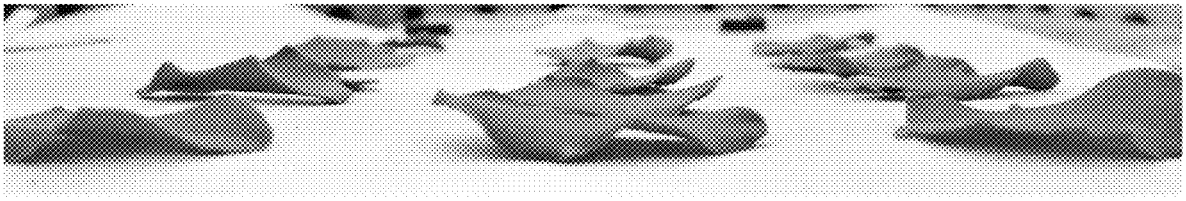

*Leaf blade*.—Elliptical in shape and brilliant, with rounded base, retuse apex (FIGS. 5B, 6A and 6B) and undulated (FIG. 6C).

*Leaf margins*.—Occasionally dentate, with pinnately primary venation. The texture of leaf upper side and backside is glabrous (FIG. 6A).

*Upper side color*.—"Greyish olive green" (RHS NN137B).

Figure 5A:
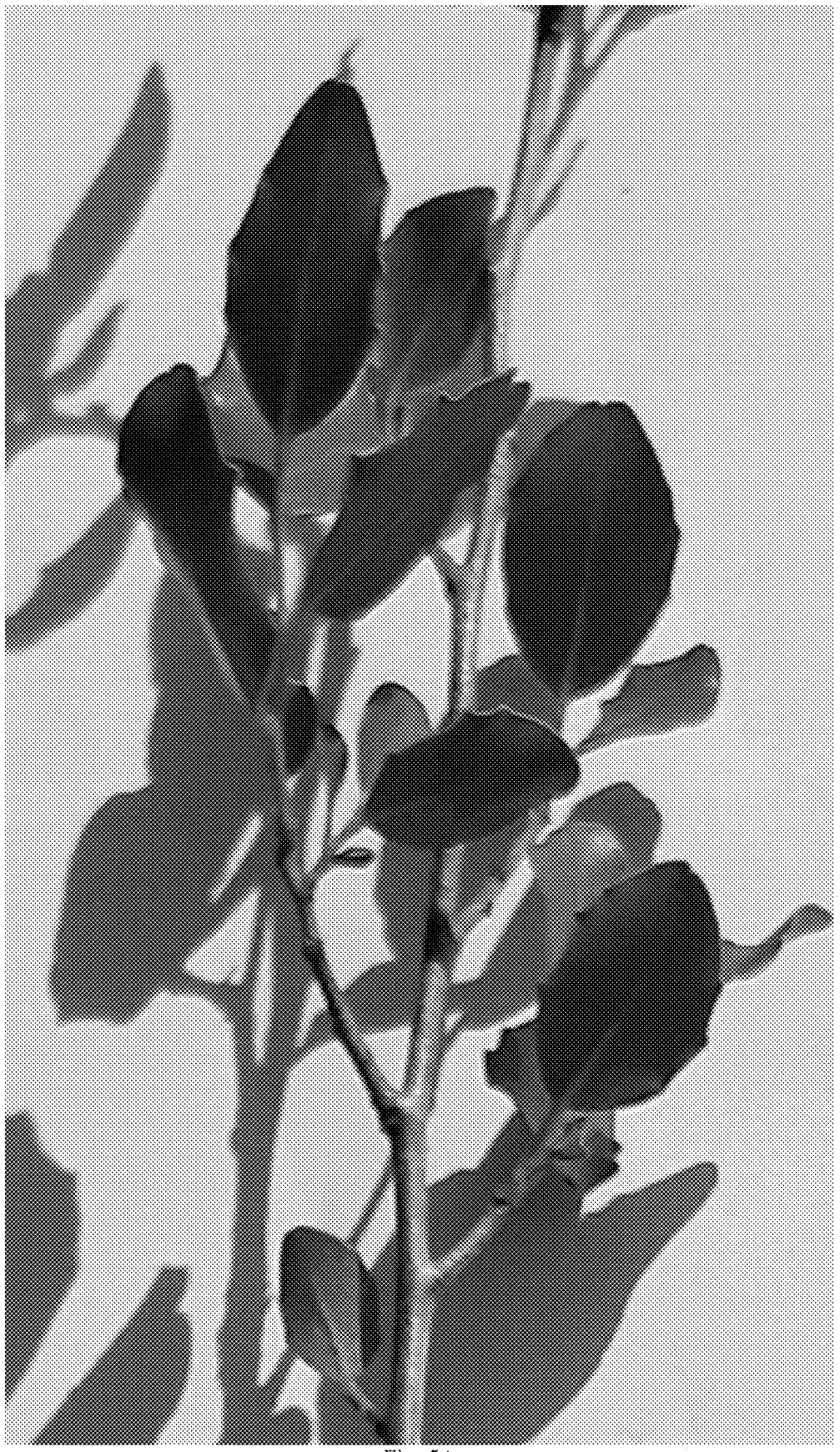
FIGS. 5A-5B are photographs of the foliar arrangement (FIG. 5A) and isolated leaves (FIG. 5B) of the variety 'DK-QSCB1326'.

*Leaf backside color*.—"Moderate yellow green" (RHS 137C) (FIG. 6B). Leaves are arranged in a helical/alternate pattern on the twigs (FIG. 5A). (according to data taken in year 2020). The leaves are petiolated. The petiole color is "Strong Yellow Green" (RHS 144 B) and their length and width are less than 2 mm. Due to their reduced size, the it was not possible to establish the petiole texture (according to data taken in year 2024).

Figure 7:
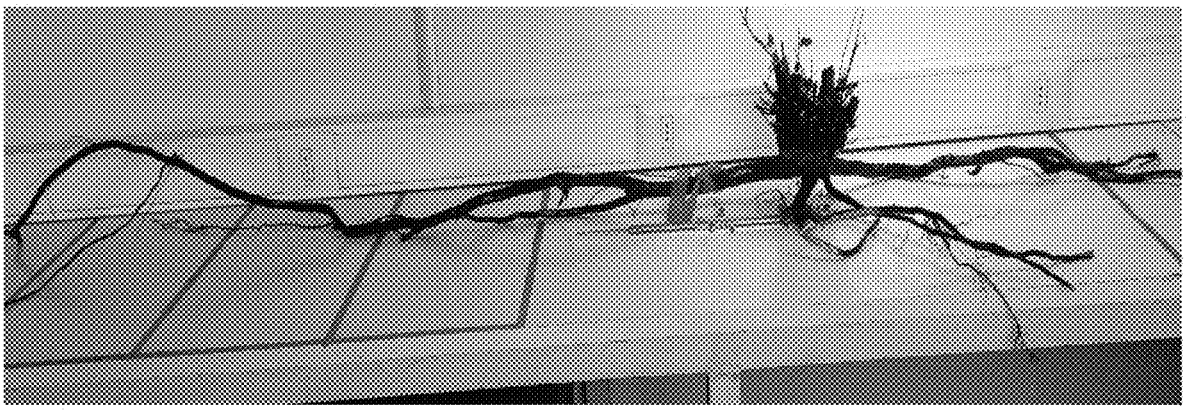
FIG. 7 is a close-up photograph of the roots of the variety 'DK-QSCB1326'.

Roots: The roots are ramified with lateral growth habit, almost cylindric in shape, glabrous without lenticels or nodules, with poor rootlets development (FIG. 7).

Flowers: The plants of this variety do not show flowers after four years growing in the field.

Disease/pest resistance: Disease resistance or susceptibility has not been assessed in this new variety.

Possible typical market uses: Extracts can be obtained from barks, leaves, branches, twigs and other plant parts. Such extracts can be chemical extracts and can be freeze-dried to obtain powdered raw materials useful as vaccine adjuvants among other pharmaceutical uses.

What is claimed is:

1. A new and distinct variety of *Quillaja saponaria* Molina plant named 'DK-QSCB1326' as described and illustrated herein.

* * * * *